(12) United States Patent
Peng et al.

(10) Patent No.: US 8,369,593 B2
(45) Date of Patent: *Feb. 5, 2013

(54) SYSTEMS AND METHODS FOR ROBUST LEARNING BASED ANNOTATION OF MEDICAL RADIOGRAPHS

(75) Inventors: Zhigang Peng, Blue Bell, PA (US); Yimo Tao, Chevy Chase, MD (US); Xiang Sean Zhou, Exton, PA (US); Yiqiang Zhan, Berwyn, PA (US); Arun Krishnan, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 358 days.

This patent is subject to a terminal disclaimer.

(21) Appl. No.: 12/787,916

(22) Filed: May 26, 2010

(65) Prior Publication Data

US 2010/0284590 A1  Nov. 11, 2010

Related U.S. Application Data

(63) Continuation-in-part of application No. 12/334,898, filed on Dec. 15, 2008, now Pat. No. 8,160,341.

(60) Provisional application No. 61/016,313, filed on Dec. 21, 2007, provisional application No. 61/181,035, filed on May 26, 2009.

(51) Int. Cl.
*G06K 9/00* (2006.01)
*A61B 6/00* (2006.01)

(52) U.S. Cl. ............................ 382/128; 382/195; 378/21

(58) Field of Classification Search .................. 382/100, 382/128, 129, 130, 131, 132, 133, 134, 162, 382/168, 181, 193, 219, 232, 254, 274, 276, 382/291, 305, 312, 195; 378/20, 5, 8, 21; 600/425
See application file for complete search history.

(56) References Cited

U.S. PATENT DOCUMENTS

| 6,674,883 | B1 * | 1/2004 | Wei et al. ...................... 382/132 |
| 6,999,549 | B2 * | 2/2006 | Sabol et al. ........................ 378/5 |
| 7,072,435 | B2 * | 7/2006 | Metz et al. ......................... 378/8 |
| 8,160,341 | B2 * | 4/2012 | Peng et al. ..................... 382/131 |
| 2005/0197567 | A1 * | 9/2005 | Qian et al. ..................... 600/425 |
| 2009/0285357 | A1 * | 11/2009 | Khamene et al. ............... 378/20 |

OTHER PUBLICATIONS

Mougiakakou et al., "Differential diagnosis of CT focal liver lesions using texture features, feature selection and ensemble driven classifiers", Artificial Intelligence in Medicine, Elsevier, NL, vol. 41, No. 1, Aug. 29, 2007, pp. 25-37.

Kalker et al., "Cardiac Image Segmentation for Contrast Agent Videodensitometry", IEEE Transactions on Biomedical Engineering, IEEE Service Center, Piscataway, NJ, vol. 52, No. 2, Feb. 1, 2005, pp. 277-286.

D. Cristinacce and T. Cootes, Facial Feature Detection Using Adaboost with Shape Constraints, In 14 th. British Machine Vision Conference, pp. 231-240, 2003.

S. Agarwal, A. Awan, and D. Roth, Learning to Detect Objects in Images via a Sparce, Part-based representation, IEEE Trans. PAMI, 26(11):1475-1490 (Nov. 2004).

(Continued)

*Primary Examiner* — Seyed Azarian
(74) *Attorney, Agent, or Firm* — Peter Withstandley

(57) ABSTRACT

Systems and methods for performing a medical imaging study include acquiring a preliminary scan. A set of local feature candidates is automatically detected from the preliminary scan. The accuracy of each local feature candidate is assessed using multiple combinations of the other local feature candidates and removing a local feature candidate that is assessed to have the lowest accuracy. The assessing and removing steps are repeated until only a predetermined number of local feature candidates remain. A region of interest (ROI) is located from within the preliminary scan based on the remaining predetermined number of local feature candidates. A medical imaging study is performed based on the location of the ROI within the preliminary scan.

21 Claims, 8 Drawing Sheets

OTHER PUBLICATIONS

T. Leung, M. Burl, and P. Perona, Finding Faces in Cluttered Scenes Using Random Labeled Graph Matching, Proc. Fifth IEEE Int'l Conf. Computer Vision, pp. 637-644, 1995.

A. Mohan, C. Papageorgiou, and T. Poggio, Example-Based Object Detection in Images by Components, IEEE Trans. PAMI, 23(4):349-361, 2001.

* cited by examiner

SYSTEMS AND METHODS FOR ROBUST LEARNING BASED ANNOTATION OF MEDICAL RADIOGRAPHS

CROSS-REFERENCE TO RELATED APPLICATION

The present application is a Continuation-In-Part Application of U.S. patent application Ser. No. 12/334,898, filed Dec. 15, 2008, which claims the benefit of U.S. Provisional Application No. 61/016,313, filed Dec. 21, 2007, which applications are hereby incorporated herein by reference in their entirety. The present application additionally claims the benefit of U.S. Provisional Patent Application No. 61/181,035, filed May 26, 2009, which application is hereby incorporated herein by reference in its entirety.

TECHNICAL FIELD

The present disclosure relates to anatomy detection and, more specifically, to robust anatomy detection though local voting and prediction.

BACKGROUND

The field of medical imaging has seen significant advances since the time X-Rays were first used to determine anatomical abnormalities. Medical imaging hardware has progressed in the form of newer machines such as Medical Resonance Imaging (MRI) scanners, Computed Axial Tomography (CAT) scanners, etc. Because of large amount of image data generated by such modern medical scanners, there has been and remains a need for developing image processing techniques that can automate some or all of the processes to determine the presence of anatomical abnormalities in scanned medical images.

Recognizing anatomical structures within digitized medical images presents multiple challenges. For example, a first concern relates to the accuracy of recognition of anatomical structures within an image. A second area of concern is the speed of recognition. Because medical images are an aid for a doctor to diagnose a disease or condition, the speed with which an image can be processed and structures within that image recognized can be of the utmost importance to the doctor reaching an early diagnosis. Hence, there is a need for improving recognition techniques that provide accurate and fast recognition of anatomical structures and possible abnormalities in medical images.

Digital medical images are constructed using raw image data obtained from a scanner, for example, a CAT scanner, MRI, etc. Digital medical images are typically either a two-dimensional ("2-D") image made of pixel elements or a three-dimensional ("3-D") image made of volume elements ("voxels"). Such 2-D or 3-D images are processed using medical image recognition techniques to determine the presence of anatomical structures such as cysts, tumors, polyps, etc. Given the amount of image data generated by any given image scan; it is preferable that an automatic technique should point out anatomical features in the selected regions of an image to a doctor for further diagnosis of any disease or condition.

One general method of automatic image processing employs feature based recognition techniques to determine the presence of anatomical structures in medical images. However, feature based recognition techniques can suffer from accuracy problems.

Automatic image processing and recognition of structures within a medical image is generally referred to as Computer-Aided Detection (CAD). A CAD system can process medical images and identify anatomical structures including possible abnormalities for further review. Such possible abnormalities are often called candidates and are considered to be generated by the CAD system based upon the medical images.

There are numerous reasons that both accuracy and speed of acquisition of image data need to be increased. For example, when using X-rays or CT imaging, it is desirable to minimize the time and area of exposure to potentially harmful radiation. By way of example, computed tomography (CT) imaging is the practice of visualizing the internal structure of a subject using a series of x-rays taken at multiple angles, the data from which may be combined and rendered by a computer system for illustrating the internal structure of the subject in three-dimensions. While CT imaging is relatively safe, it does involve exposure to ionizing radiation, which could become harmful in patients. Accordingly, it is generally considered prudent to limit the acquisition of image data to a particular field of the subject's body. By scanning only this field, the patient's exposure to ionizing radiation can be limited and the time needed to acquire the image reduced. Moreover, by limiting the scanning field, it is possible to acquire the desired image data more quickly and with less use of resources than if the entire body was scanned.

It is therefore important to be able to correctly identify the scanning field so that the resulting CT image captures the desired structural data. If the scanning field is selected to be sufficiently large, then there is less risk of missing pertinent structural data. However, the more precise the field is, the faster the scan can be performed and the less the subject is exposed to potentially harmful ionizing radiation. Accordingly, it is desirable to select a precise scanning field that is only as large as is necessary to capture the desired structural data.

In order to set the scanning field, often the CT scanner is used to produce one or more topograms of the subject's body. A topogram is a scout image that may be used to establish where the target organs are located within the subject's body so that the scanning field may be precisely selected. The topogram appears similar to a conventional radiograph, where the outline of the subject's body may be seen with certain organs and anatomical features superimposed thereon.

Presently, the scanning field is manually determined by a human operator such as a radiology technician. The human operator uses learned knowledge of human anatomy to identify the organs to be imaged and then selects the scanning field to be scanned in detail. However, this manual determination may take an amount of time that is noticeable to the subject, and as such, there is a greater possibility that the subject may shift position between the acquisition of the topogram and the acquisition of the CT scan within the manually determined scanning field. Accordingly, the manually determined scanning field must be selected with wide margins to allow for subtle movement. Moreover, the manually selected scanning field may be slightly different each time a CT scan is performed and thus multiple CT scans, such as follow-up studies of the same patient and/or cross-patient comparisons, may be more difficult to compare owing to the inherent inconsistency of the manual field selection. The description of CT image capture and its limitations is merely exemplary, as similar issues surround the use of other imaging modalities as well.

The amount of medical image data produced is constantly growing. In addition to the above-described difficulties in correctly identifying a scanning field for a medical image study, annotation of the ever-increasing number of medical images is an overwhelming task. Manually annotating these images is costly and error-prone, which means that automatic annotation algorithms are needed and must to be able to perform the task reliably and efficiently. This is particularly true for radiograph images, although similar issues exist for other imaging modalities.

A great challenge for automatic medical image annotation is the large visual variability across patients in medical images from the same anatomy category. In some cases, diseases or artifacts can render an anatomy unrecognizable even by human eyes. Additionally, an automatic annotation system must be able to automatically recognize the projection view of for example, chest radiographs.

Therefore there is a need for improved systems and methods to facilitate robust anatomy detection in medical images, and systems and methods for automatically annotating medical images such as radiograph images.

SUMMARY OF THE INVENTION

A method for locating a region of interest includes acquiring at least one preliminary scan. A set of local feature candidates is automatically detected from the at least one preliminary scan. The accuracy of each local feature candidate is assessed using multiple combinations of the other local feature candidates and removing a local feature candidate that is assessed to have the lowest accuracy. The assessing and removing steps are repeated until only a predetermined number of local feature candidates remain. A region of interest (ROT) is located from within the at least one preliminary scan based on the remaining predetermined number of local feature candidates. A medical imaging study is performed based on the location of the ROI within the at least one preliminary scan.

The preliminary scan can be a scout image that includes a two-dimensional representation of a subject being scanned. The method can include annotating the at least one preliminary scan to identify the location of each of the predetermined number of local feature candidates. The medical imaging study can be a CT scan.

The local feature candidates can represent potential anatomical landmarks. The local feature candidates can be automatically detected from the preliminary scan by identifying regions of the preliminary scan that appear to be known anatomical landmarks. The set of local feature candidates may include multiple local feature candidates that appear to be the same anatomical landmark.

The accuracy of each local feature candidate may be assessed by using each combination of other local feature candidates as a voting group, wherein each voting group votes for the each local feature candidate by judging the degree to which the each local feature candidate represents a corresponding local feature wile assuming that the voting group accurately represents corresponding local features. Each voting group may include 1, 2, 3, or more other local feature candidates.

Locating a region of interest (ROT) from within the preliminary scan based on the remaining predetermined number of local feature candidates may include using the remaining predetermined number of local feature candidates as a frame of reference to structurally register the preliminary scan and then finding the region of interest (ROI) within the preliminary scan based on the structural registration.

Each of the multiple combinations of the other local feature candidates may make up a voting group that votes for each local feature candidate in assessing their accuracy and for each iteration of repeating the assessing and removing step. A local feature candidate may be assessed to have the lowest accuracy when it has a lowest vote from among maximum votes received by each of the multiple combinations of the other local feature candidates.

For each iteration of repeating the assessing and removing step, a local feature candidate may be assessed to have the lowest accuracy when it is has a sudden reduction in vote value, as determined by examining the mean of good votes from a most recent iteration.

A method for annotating a medical image includes receiving a medical image. A set of local feature candidates is automatically detected from the medical image. Which of the local feature candidates represent a worst candidate is determined by having a plurality of groups of the local feature candidates vote on each individual local feature candidate, and removing the worst candidate from the set of local feature candidates. The voting and removal are repeated such that one feature candidate is removed from the set at each iteration, until there are only a predetermined number of remaining feature candidates. The medical image is annotated to identify the location of each of the remaining feature candidates.

The local feature candidates may represent potential anatomical landmarks. Voting may be performed by using each combination of other local feature candidates as a voting group. Each voting group may vote for the each local feature candidate by judging the degree to which the each local feature candidate represents a corresponding local feature wile assuming that the voting group accurately represents corresponding local features.

Selecting the scanning field based on the remaining feature candidates may include finding a region of interest (ROI) within the medical image based on the remaining feature candidates and selecting the scanning field to include the region of interest (ROI).

The region of interest may be found within the medical image by using the remaining feature candidates as frame of reference to structurally register the medical image and then finding the region of interest (ROI) within the medical image based on the structural registration. The region of interest (ROI) to be found may be manually selected by a user.

A computer system includes a processor and a program storage device readable by the computer system, embodying a program of instructions executable by the processor to perform method steps for locating a region of interest. The method includes acquiring a medical image; automatically detecting a set of local feature candidates representing potential anatomical landmarks from the medical image; assessing the accuracy of each local feature candidate using multiple combinations of the other local feature candidates and removing a local feature candidate that is assessed to have the lowest accuracy; repeating the assessing and removing step until only a predetermined number of local feature candidates remain; locating a provided region of interest (ROI) from within the medical image based on the remaining predetermined number of local feature candidates.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION OF THE INVENTION

Figure 1:
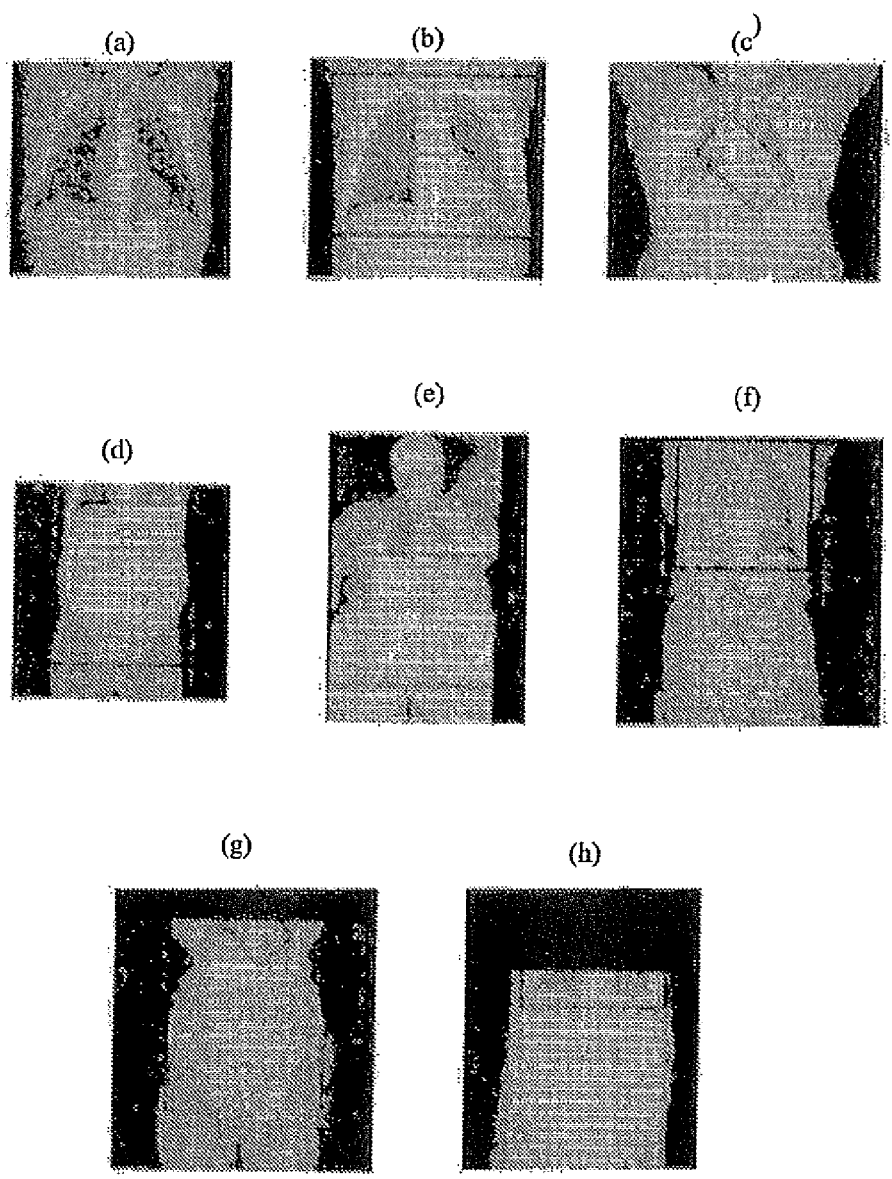
FIGS. 1(a)-(h) are examplary CT topograms that may be used to automatically determine an appropriate scanning field according to exemplary embodiments of the present disclosure.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary imaging modality. It will be appreciated, however, that data from any type of imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Exemplary embodiments of the present invention seek to provide an approach for automatically selecting a scanning field within a medical image for the localization of a medical image study. By automatically selecting the scanning field, rather than having the field manually selected by a human operator, the process of acquiring a medical image may be sped up, made more reliable, and/or provide for a greater level of consistency and/or repeatability.

FIGS. 1(a)-(h) are example CT topograms that may be used to automatically determine an appropriate scanning field according to exemplary embodiments of the present invention. In these topograms, the outline of the subject may be seen with various anatomical structures superimposed thereon. Where present, the determined scanning fields are displayed with black boxes.

The topograms may be relatively, low resolution, for example, each image may be 512 pixels by 512 pixels. Because the topogram can be of a relatively low resolution and does not require the sophisticated three-dimensional rendering of a CT scan, the topogram may be acquired relatively quickly and with minimal exposure to ionizing radiation.

Automatically identifying the scanning field may involve registering the topogram against a known anatomical map. Thus proper identification of the scanning field may depend on finding a strong relationship between the anatomical configuration of the subject and that of the anatomical map. One key problem in identifying the scanning field from within a topogram is the fact that the relative size and position of human anatomy can vary widely from subject to subject and from time to time. These variations may cause many heuristic approaches to fail to be able to correctly locate the desired structural features from within the topogram. For example, an obese patient with hands up, as illustrated in FIG. 1(e) may be difficult to automatically detect a scanning field for where the method of registering the structure of the subject depends on skin or head/neck detection.

In addition to variations in the subject's size and proportions, disease may enlarge, shrink, or change the relative position of one or more anatomical structures for which registration depends. Moreover, in addition to normal variations between subjects, many subjects may have an unusual anatomical structure owing to prior surgical treatment and/or congenital defect. For example, FIG. 1(f) is a topogram of a subject with a collapsed or resected lung. It would be difficult to automatically determine a scanning area on such a patient when registration utilizes active shape/appearance modeling such as performing registration based on a determined location of the lung. Additionally, in many partial-body topograms, as much as 80% to 90% of certain anatomical features can be out of the field of view of the topogram. An example of this may be seen in the topogram image of FIGS. 1(g) and (h).

Accordingly, it may be difficult to automatically identify a scanning field with a level of accuracy that is at least as good as when manually identified.

One possible solution to this problem would be to utilize a local feature based approach to register the topogram, for example, as discussed in D. Cristinacce and T. Cootes, *Facial Feature Detection Using Adaboost with Shape Constraints, In* 14*th. British Machine Vision Conference*, pages 231-240, 2003, which is herein incorporated by reference. In such a solution, shape models are formed to recognize various geometric structures that may be found within the topogram. There may be multiple shape models for each structure so that a particular anatomical structure may be identified even if its appearance is dissimilar to the most common configuration, so long as these is an existing shape model available that is sufficiently similar. According to this approach, multiple hypotheses of each local feature may be screened using the predetermined shape models and a winning hypothesis may be determined for each feature. Missing features may then be predicted using the model.

If a feature detector produces only false hypotheses, the shape model may reject all configurations and thus insufficient structural identification may be provided. Unfortunately, where patients have significant structural abnormalities such as tumors and/or full organ resection, local feature based registration may fail to provide adequate structural identification.

In an attempt to solve the problem of detecting anatomical structure in the even of partial obstruction or the case where a portion of a structure is beyond the field of view, sparse, part-based representation may be used to identify local features, for example, as discussed in S. Agarwal, A. Awan, and D. Roth, Learning to Detect Objects in Images via a Sparce, Part-based representation, *IEEE Trans. PAMI*, 26(11):1475-1490, 2004, which is herein incorporated by reference. Here, a global constraint may be imposed through the learning process of creating shape models. Thus, structural identification may be possible in the presence of mild occlusion. However, severe occlusion, for example, in the range of 80% to 90%, may still prevent proper detection of anatomical structure. Moreover, the accuracy of this approach, which may be based on a single consolidated global decision, may not satisfy the local accuracy requirement of the topogram application.

In performing structural identification using local features, graph matching may be used to evaluate competing constellations of local features, for example, as discussed in T. Leung, M. Burl, and P. Perona, *Finding Faces in Cluttered Scenes Using Random Labeled Graph Matching, Proc. Fifth IEEE Intl Conf. Computer Vision*, pages 637-644, 1995, which is herein incorporated by reference. Here, a graph may be constructed to model the mutual dependency in terms of mean and variance of distance. Pruning strategies may be applied to limit the number of candidate constellations. For example, the local detector confidence may be used to elect a set of "strong features" as leads.

However, such techniques may result in false detections that have a high level of confidence.

Other techniques may perform pedestrian detection using separate support vector machine (SVM) classifiers to detect body parts such as heads, arms and legs, for example, as discussed in A. Mohan, C. Papageorgiou, and T. Poggio, *Example-Based Object Detection in Images by Components, IEEE Trans. PAMI*, 23(4):349-361, 2001, which is herein incorporated by reference. Here, a second SVM classifier may integrate the detected parts to make a decision as to whether a person has been detected. Such techniques may be useful even in the event of partial occlusion or where there is little contrast between people and backgrounds. However, such techniques may not be useful in identifying a subset of valid local features to draw the regions of interest, as may be required to automatically identify a scanning field, as in such techniques, the black-box nature of the SVM classifier gives no information as to which local features might be invalid.

As discussed above, before the CT examination is performed, a topogram is acquired to aid in the determination of a scanning field. The scanning field generally coincides with a region of interest (ROI) that includes, for example, an organ that is to be examined. An ROI may be defined by a few well-known anatomical landmarks. For example, the abdomen ROI may range from the upper dome of the diaphragm to the symphysis pubis. In FIG. 1, the ROIs, and thus the scanning fields, may be represented as a black box, for example, as seen in FIG. 1(b), (c), (d), (e), (f), (g), and (h). The ROIs may have boundaries that are parallel and perpendicular to the sides of the topogram, as seen in FIGS. 1(b), (d), (e), (f), and (h) or the ROIs may be slanted as seen in FIGs. (c) and (g). Moreover, the ROIs may be fully contained within the topogram, as seen in FIGS. 1(b), (c), and (d) or the ROIs may be partially out of view as seen in FIGS. 1 (g) and (h).

Examples of common ROIs may include the lungs, heart, abdomen, liver, pelvis, etc.

Exemplary embodiments of the present invention seek to automatically detect the set of ROIs, $\Re = \{r_k\}$ from the topogram, even where one or more of the ROIs are only partially present. Then the scanning field for the CT study may be automatically defined based on the detected ROIs. In detecting the ROIs, a local feature-based approach may be used. This may be accomplished by identifying a set of landmarks and judging the accuracy of each landmark by relation to a group of other landmarks. This judgment is referred to herein as a "vote" and each landmark is voted upon by one or more combinations of other landmarks that are referred to herein as "voting groups."

Thus, the local features may be used as the set of anatomical landmarks, X, where $|X|=N$. A local voting algorithm may then be used to produce an indicator array $\Omega = \{\omega_i\}$, where $|\Omega|=N$ and $\omega_i \in \{0,1\}$, and where:

$$\omega_i = \begin{cases} 1 & \text{if landmark } x_i \text{ is elected,} \\ 0 & \text{if landmark } x_i \text{ is voted out.} \end{cases} \quad (1)$$

The local voting process may be formulated as follows:

$$\Omega^* = \text{argmax} \sum_{i=1}^{N} \omega_i \times \Gamma(x_i | X \setminus x_i) \quad (2)$$

where $\Gamma(x_i|X\setminus x_i)$ represents the best "vote" received by $x_i$, $\|\Omega\|_1 = \sum_{i=1}^{N} \omega_i$, and M<N is the desired number of remaining landmarks. Voting is described in greater detail below.

As used herein, $\tilde{X}$ denotes the set of elected landmarks $\tilde{X} = \{x_i | \omega_i = 1\}$. The result of the voting is to predict the ROIs using a subset of the elected landmarks $\tilde{X}$. Each ROI $r_k$ may be predicted according to the formula:

$$r_k = \wp_k(\tilde{X}) \quad (3)$$

where $\wp_k(\ )$ first selects a best subset from $\tilde{X}$, and then predicts ROI $r_k$. This ROI prediction mechanism is described in greater detail below.

Figure 2:
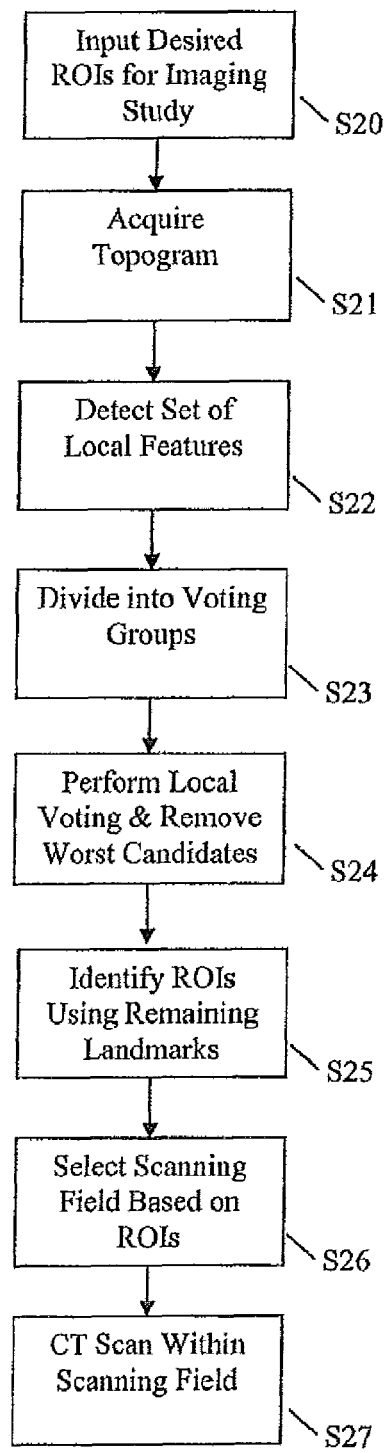
FIG. 2 is a flow chart illustrating a method for automatically detecting a scanning field according to an exemplary embodiment of the present disclosure.

FIG. 2 is a flow chart illustrating a method for automatically detecting a scanning field according to an exemplary embodiment of the present invention. First, the topogram is acquired (Step S21). As discussed above, the topogram is a scout image that includes a two-dimensional representation of the subject. The topogram may be acquired using a particular modality of the same imaging device that is used to acquire the detailed medical image data. Next, a set of local features are detected (Step S22). Each local feature may be an anatomical landmark that is observable from the topogram. The set of local features may be a redundant set of local features, X, that are detected with multiple hypotheses. This is to say that there may be multiple local features detected for the same anatomical landmark whereby each of the local features is obtained based on a different set of assumptions for identifying the feature.

Next, the set of local features X, or landmarks, may be divided into subsets of spatially consistent local features $\hat{X}$, or voting groups, where $\hat{X} \subset X$ (Step S23). The goal may be to select a subset of most reliable features $\hat{X}$ and predict the ROIs and thus the scanning field, based on the set of most reliable features $\hat{X}$. Exemplary embodiments of the present invention find the subset of most reliable features $\hat{X}$ by removing each of the worst match landmark features until all that is left is the subset of most reliable features. Thus, rather than attempting to find a single best constellation of landmarks that may be indicative of the ROI, exemplary embodiments of the present invention pare away the worst matches. This may be especially beneficial, as it is possible for a poor landmark constellation to be incorrectly identified as a best match, as is described in detail below.

This assessment as to the quality of each landmark candidate is referred to herein as "local voting." Accordingly, after the landmarks have been divided into the voting groups $\hat{X}$(Step S23), local voting is performed to assess the relative quality of each candidate (Step S24).

As discussed above, each landmark is considered a candidate for the most reliable feature set. The quality of a candidate is voted upon by voting groups formed by other landmarks.

Each landmark may participate as an individual voter and may also form voting groups with other landmarks. Each "vote" may be a binary variable, for example, a high vote may equal "1" and a low vote may equal "0" or each vote may be a real number, for example, a conditional probability. The higher the vote, the more likely the candidate is to be a good feature.

Assuming the size of each voting group is L, each landmark may receive $C_{N-1}^{L}$ number of votes. A voting group may be small, for example, with L=1, 2, or 3. For example, a voting group may include only two other landmarks. Alternatively, each voting group may include a large number of landmarks, with L≥4. Exemplary embodiments of the present invention may be explained in terms of voting groups of 2 landmarks for the purposes of simplifying the explanation so that greater attention may be paid to the reasoning strategy behind the voting. However, it is to be understood that the voting groups may be made up of any number of other landmarks, and it may also be possible to utilize voting groups of dissimilar size.

In voting (Step S24), each voting group may designate each candidate with a high vote or a low vote. However, each voting group may itself be either a "good" voting group or a "bad" voting group. A voting group is "good" if all of its members are good voters, and a voting group is "bad" if all of its members are bad voters. A voter is good if it can correctly give a good candidate a high vote and a bad candidate a low vote thereby productively helping to determine the ROI. Meanwhile, a voter is bad if it either fails to give a good candidate a high vote or fails to give a bad candidate a low vote thereby being counterproductive in determining the ROI. There are many reasons why a voter would be counterproductive, and some of these reasons are discussed in detail below. It may also be possible that for a given voting group, some voters are good and others are bad. Such a voting group may be considered a "mixed group."

As discussed above, where the ROI is attempted to be found using a single best constellation of landmarks, the possibility exists that bad landmarks are selected for use because of various voting behavior models that tend to allow for bad landmarks to be judged positively. Exemplary embodiments of the present invention can avoid this trapping by removing bad candidates form consideration prior to selecting the landmarks to use.

As discussed above, there are various voting behavior models that would tend to rate bad candidates positively when not using exemplary embodiments of the present invention. For example, according to the naive model, the "naive" voter group would assign a low vote to all candidates, regardless of whether they are good or bad. According to the Mafia model, however, there can be a collection of candidates/voters that are in truth bad, but tend to give high votes to other members of the same collection. In this way, bad voters may make each other look good. This may happen, for example, when a set of erroneous landmarks form a legitimate constellation. However, a good voter may be used to veto any bad candidate. According to the Mafia plus corrupted citizen model, however, it is possible that a voter that is not within the collection of candidates bad that self-validate, can also provide a high vote to the collection of bad candidates.

In light of these various voting behavior models, exemplary embodiments of the present invention "peel away" bad candidates so that they cannot be used to vote on remaining candidates. While this may be achieved using any number of strategies, two exemplary strategies are discussed in detail below. It is to be understood that similar strategies may be used based on the two strategies explained below. For example, elements of each strategy may be combined to provide additional strategies.

According to a first strategy, a "weakest link" is iteratively removed from the pool of voters. Each candidate receives votes from various combinations of the other candidate-voters. A maximum vote is the highest vote score attributed to the candidate under review from among the voters. Thus, this value is the best vote that the candidate received. In each iteration, the maximum votes received by all remaining candidates are compared. The candidate whose maximum vote is minimum across all the remaining candidates is removed. The candidate whose best vote is minimum may be considered a "weakest link" and may therefore be removed. This process may be repeated until the number of the remaining candidates reaches a predetermined value M. Thus it is assumed that there are at least M good candidates and that all of the bad candidates can be removed as weakest links. This weakest link removal strategy may work well when faced with candidates of the naive behavior model.

Exemplary pseudo code for implementing the weakest link is provided below in Table 1:

TABLE 1

```
for each candidate x_i do
    for each combination of X\x_i do
        Compute the vote of x_i
    end for
    sort all the votes received by landmark x_i (The sorted array is
    defined by γ_{x_i}).
end for
repeat
    x̌ = arg min_{x_i} max γ_{x_i}
    Remove x̌ and all votes involved with x̌.
until Only M candidates are left
```

According to a second strategy, a transverse pointer h is used to progress forward and backward checking the $h^{th}$ maximum vote for each candidate as h progresses.

In the forward stage, h moves along the sequence $\{C_{j-1}^L + 1 | j = L+1, \ldots, N+1\}$, where the size of the voting group and candidates set are L and N, respectively. The $h^{th}$ maximum vote for each candidate may be checked. A substantial vote drop found before h=L+1 may indicate that the corresponding candidate is a member of a mafia collection. A vote drop is a sudden reduction in a vote value. A vote drop may be determined, for example, as described in detail below.

Accordingly, the candidate that has experienced a vote drop may be removed from consideration. After removal, h may start to go backward to prune other members of the mafia collection. This process may be repeated until there are no more vote drops found and thus no more mafia collections. When L=2, the sequence that h traverses, first forward and then backward, may be called the Lazy Caterer's Sequence or the central polygonal numbers, hence, this strategy may be called the Lazy Caterer's strategy.

Exemplary pseudo code for implementing the Lazy Caterer's strategy is provided below in Table 2:

TABLE 2

```
for each candidate x_i do
    for each combination of X\x_i do
        Compute the vote of x_i
    end for
    sort all the votes received by landmark x_i (The sorted array is
    defined by γ_{x_i}).
end for
```

$$T(\gamma_{x_i}) = \frac{\sum_{x_i} \max(\gamma_{x_i})}{N}$$

```
j_max = L + 1
for j from j_max to N/2 - 1 do
    h = C_{j-1}^L + 1
    x̌ = argmin_{x_i} γ_{x_i}[h]
```

TABLE 2-continued

```
    if γ_{x̌}[h] < T(γ_{x_i})/3 then
        if j_max < j then
            j_max = j
        end if
        Remove all votes involved with x̌.
        j = j - 1.
        N = N - 1.
        Continue
    end if
```

$$T(\gamma_{x_i}) = \frac{\sum_{x_i} \gamma_{x_i}[h]}{N}$$

```
end for
```

For the pseudo code of Table 2, the $$\frac{T(\gamma_{x_i})}{3}$$

term is an adaptive threshold for detecting the substantial vote drop, where $T(\gamma_{x_1})$ is the mean of the good votes in the last iteration. The selected denominator "3" of this term may be changed to suit the needs of the particular vote function and/or problem being solved.

The Lazy Caterer's strategy may thus be used to overcome the problem associated with the naive model, the mafia model, and/or the mafia plus corrupted citizen model. Accordingly, the above-described weakest link strategy and/or the Lazy Caterer's strategy may be used to perform local voting to assess the relative quality of each candidate (Step S24). In this step, as described above, weakest voters are removed until there are only a predetermined number of voters remaining. These remaining voters may then be used to automatically identify the desired ROIs from within the topogram image (Step S25). As the ROIs represent regions of interest within the body of the subject that are to be the focus of the imaging study, the medical practitioner may input the desired organs and/or other anatomical structures that are to be treated as ROIs (Step S20). For example, if the medical practitioner desires that the lungs be imaged, the medical practitioner can establish the lungs as ROIs. This selection of ROIs may occur prior to the acquisition of the topogram image (Step S21) where it is desired that the length of time between the acquisition of the topogram (Step S21) and the acquisition of the medical image study (Step S27) be minimized, however, it may also be possible to select the desired ROIs after the topogram is acquired.

After the ROIs have been automatically identified within the topogram (Step S25), the goal is to perform the medical image study in such a way as to include the identified regions of interest. However, the scanning field often has a more normal shape than the shape of the one or more ROIs that are to be imaged. For example, the scanning field may be a rectangle. Accordingly, after the ROIs have been identified, a scanning field may be automatically selected that includes the identified ROIs (Step S26). Then, the medical image study may be performed within the selected scanning field (Step S27). The medical image study may be, for example, a CT scan.

Figure 3:
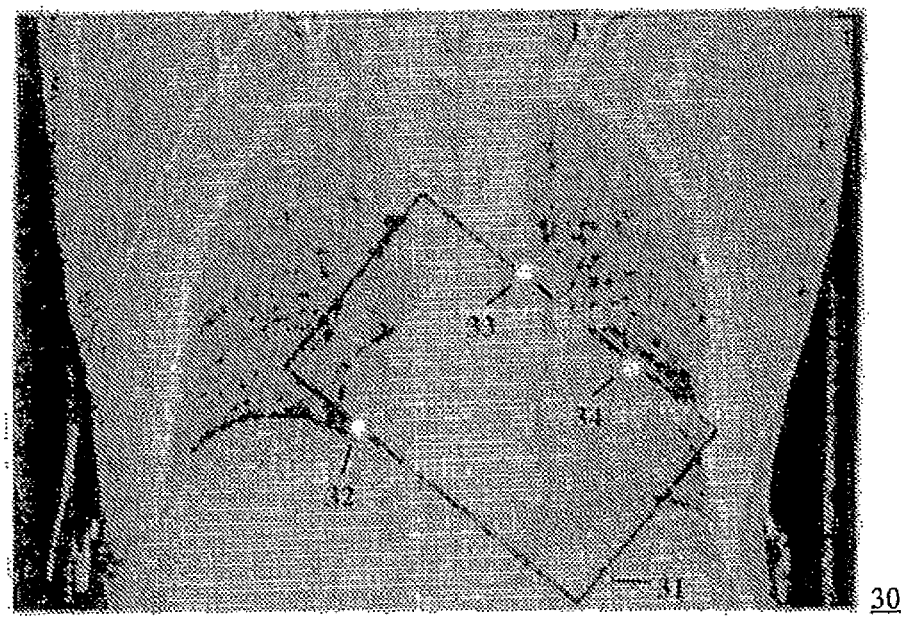
FIG. 3 is an examplary topogram image where a scanning filed box is drawn to include the heart as an ROI.

The scanning field may be automatically selected based on the ROIs either in accordance with a predetermined protocol or by drawing a box to cover the ROIs with the smallest possible size. In drawing the box, any angle may be used to achieve the smallest possible sized box that includes the full ROIs. Where the scanning field box is drawn in accordance with a predetermined protocol, the protocol may provide for drawing the box that crosses predetermined landmarks. For example, when the ROI in question is the heart, a scanning field box 31 may be drawn to cross the heart corner landmark 32, the heart base landmark 33, and the heart lower landmark 34, as can be seen in FIG. 3, which is an example of a topogram image 30 where the scanning field box 31 is drawn to include the heart as an ROI.

Similarly, where the lung and heart are the ROIs to be imaged, the scanning field box may be drawn to cover the following seven landmarks: left lung corner, right lung corner, left lung apex, right lung apex, heart corner, heart base, and heart lower. Where the ROIs include the abdomen, liver, and pelvis, the scanning field box may be drawn to cover the following four additional landmarks: the left diaphragm dome, right diaphragm dome, liver base, and symphysis pubis.

Voting according to exemplary embodiments of the present invention will now be described in greater detail. However, it is to be understood that the voting process discussed herein is an example of a voting process that may be used, and that those of ordinary skill in the art may be able to utilize other voting processes.

The vote received by a candidate $x_i$ may be denoted by $\eta(x_i|X_v)$ where $X_v$ is a voting group. The vote may be defined as a likelihood between candidate $x_i$ and its estimation $v_i$ coming from the voting group. The likelihood function may be modeled as a multi-variance Gaussian function, for example, as follows:

$$\eta(x_i \mid X_v) = \frac{1}{(2\pi)^{\frac{N}{2}} |\Sigma|^{\frac{1}{2}}} e^{-(x_i - v_i)^T \Sigma^{-1} (x_i - v_i)} \quad (4)$$

where $\Sigma$ is the covariance matrix, and the estimation $v_i$=M×[$X_v$]. Here [$X_v$] is the array of the x, y coordinate of $X_v$ and M is the transform matrix computed from a training set.

In voting, the erroneous landmarks may be considered to be outliers and the remaining good landmarks may be considered to be inliers. Thus, the process of selecting inliers may be considered an outlier removal problem.

As discussed above, prediction of the ROIs $r_k$, may be performed by selecting the best subset $\hat{X}$ from the landmarks $X$ and using only the best subset to compute the ROIs. The ROIs $r_k$, may be represented by a set of parameters $\theta_k$, which may be computed according to the following equation:

$$\theta_k = \xi \times [\hat{X}] \quad (5)$$

where [$\hat{X}$] is the array of the x, y coordinates in $\hat{X}$.

The transformation matrix $\xi$ may be computed from the training sets by the given ground truth parameters $\theta_k^*$ from the set of landmarks X' by using the minimum error criterion to estimate $\xi$ for example:

$$\xi = (\theta_k^* \times [X']^T)([X'] \times [X']^T)^{-1} \quad (6)$$

The covariance matrix may also be computed from [X]' and $\theta_k^*$. The covariance matrix, once computed, may then be used to determine whether a landmark subset $\hat{X}$ is good or bad. The landmark subset with the minimum covariance value may then be used to predict the location of the ROIs.

The present disclosure provides, among other things, an algorithm for automatic annotating medical radiographs. This algorithm automatically recognizes the projection view of chest radiographs, and can be readily integrated with a PACS workstation to support optimized image display for improving the PACS radiography workflow. While chest radiographs are referred to often in this disclosure, because of the generality and scalability of the proposed algorithm, the present disclosure also demonstrates the capability of the disclosed systems and methods to robustly and efficiently annotate medical radiographs containing anatomy content other than chest.

One great challenge for automatic medical image annotation is the large visual variability across patients in medical images from the same anatomy category. In some cases, diseases or artifacts can render a particular patient's local anatomy unrecognizable even to trained human eyes.

Figure 5:
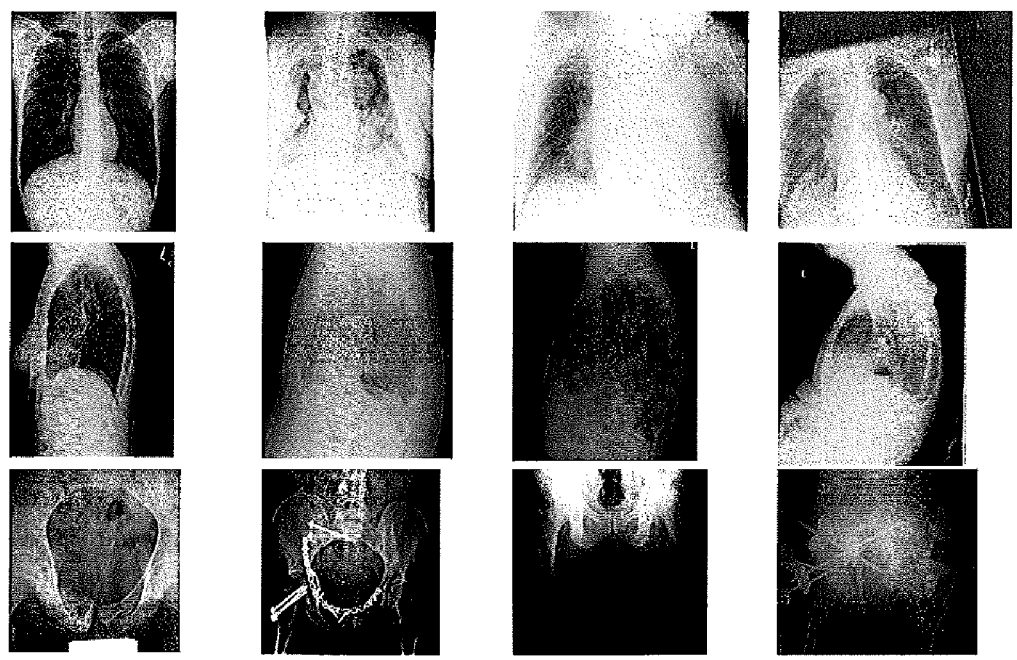
FIG. 5 is a set of exemplary radiographs that may be used for automatic annotation according to an embodiment of the present disclosure.

FIG. 5 shows a series of exemplary medical radiographs from different anatomy classes. The first and second rows in FIG. 5 show examples of posteroanterior/anteroposterior (PA-AP) and lateral (LAT) chest radiographs, respectively. Because of the differences of individual body conditions, patient ages, and appearances of disease or artifacts, the same class PA-AP and LAT images may present very high intra patient variability. The third row of FIG. 5 shows another example of images from the pelvis class with considerable visual variance caused by contrast difference and artifacts.

Most existing methods for automatic medical image annotation are based on different types of image content descriptors, separately or combined together with different classifiers. One known method of automatic annotation described in Hiller et al., "Performing image classification with a frequency-based information retrieval schema for ImageCLEF 2006," in *Working Notes of the 2006 CLEF Workshop*, 2006, used weighted combination of different global and local features to compute the similarity score between the query image and reference image in the training database. The Muller annotation strategy was based on the GNU Image Finding Tool image retrieval engine. Another known method of automatic annotation, described by Deselaers and Ney, "Deformations, patches, and discriminative models for automatic annotation of medical radiographs," *Pattern Recognition Letters*, vol. 29, pp. 2003-2010, 2008, used a bag-of-features approach based on local image descriptors. The bags of local image features are classified using discriminative classifiers. Another known method, described in Tommasi et al. "Discriminative cue integration for medical image annotation," *Pattern Recognition Letters*, vol. 29, pp. 1996-2002, 2008, extracted SIFT features from downscaled images and used similar bag-of-features approach. A modified SVM integrating the bag-of-features and pixel intensity features was used for classification.

More specifically, for the task of recognizing the projection view of chest radiographs, known methods and systems include: (1) using a linear discriminant classifier with two features extracted from horizontal axis projection profile; (2) computing the cross-correlation coefficient based similarity of a chest image with manually defined template images generated; (3) using down-scaled image pixels with four distance measures along with K nearest neighbor (KNN) classifier; (4) using a neural network (NN) classifier working on down-sampled images; (5) two major stages including region of Interest (ROI) extraction, and then classification by combined Gaussian mixtures classifier and a NN classifier using features extracted from ROI. An accuracy of 98.2% was reported on a large test set of 3100 images. Although such methods mentioned above can perform well on high quality or normal images, the last 1% of accuracy gain by robustly recognizing challenging cases as shown in FIG. 5 still calls for better solutions. More importantly, in order to build a fully automatic system to be integrated into CAD/PACS (Computer Aided Detection/Picture Archiving and Communication System) for identification of PA-AP and LAT chest radiographs, requires the system to filter out radiographs containing anatomy contents other than chest. Therefore, the task becomes a three-class classification problem, i.e., identifying images of PA-AP, LAT, and OTHER, where "OTHER" are radiographs of any other anatomies (e.g., head, pelvis, hand, spine, etc.). Currently 30-40% of radiographies have their projection/orientation information mislabeled or missing in the DICOM header. However, this real world problem (considering all possible "OTHER"s) has not yet been addressed by the prior art.

Figure 6:
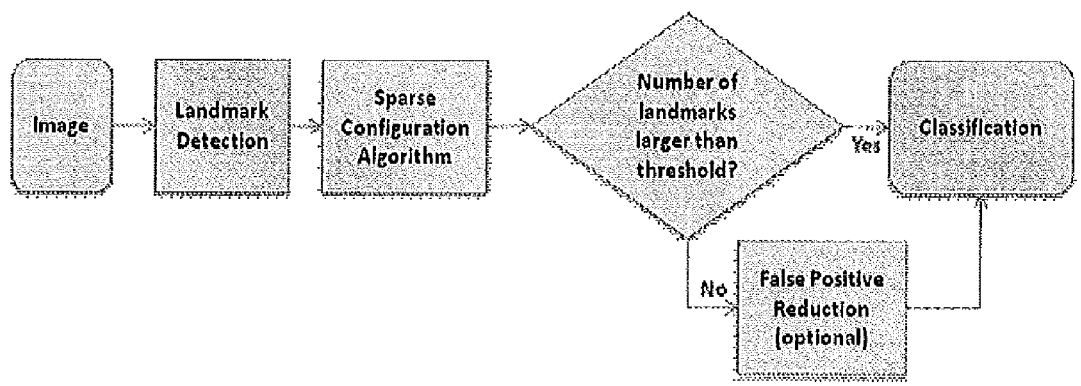
FIG. 6 is a flow chart illustrating a method for automatically annotating a medical image according to an embodiment of the present disclosure.

The present disclosure describes a novel learning-based algorithm based on robust aggregation of learned local appearance evidences for parsing and annotation of medical images. FIG. 6 shows an overview of an algorithm according to an embodiment of the present disclosure. The algorithm is designed to first detect multiple focal anatomical evidences within a medical image. This is achieved through a learning-by-example landmark detection algorithm that performs simultaneous feature selection and classification at several scales. A second step is performed to eliminate inconsistent findings through a sparse configuration algorithm where consistent and feasible detected local evidence will be retained while outliers removed. Finally, a reasoning module assesses the evidences, i.e., remaining landmarks, to determine the final content/orientation of the image. Depending on the classification task, a post-filtering component may also be included to reduce false positive identification.

In the area of medical image analysis, anatomical landmark detection often plays a fundamental and critical role. High level medical image analysis and understanding usually starts from the identification and localization of anatomical structures. Therefore, accurate and robust anatomical landmark detection becomes critical to the performance of medical image understanding.

The landmark detection module in this work is adapted to exploit anatomical context and scale of each detected landmark. This is achieved by an adaptive coarse-to-fine implementation in the scale space, and allowing for flexible handling of the effective field of view for each landmark. For example, context may only come from below a certain landmark given a particular application (e.g., lung apex in Chest X-Ray). Joint detection of multiple landmarks improves the overall accuracy and stability.

The detected landmarks in the first step may be redundant and erroneous. Knowing that the possible locations of landmark points in the human body are rather limited, the systems and methods of the present disclosure take advantage of this geometric property in order to eliminate the erroneous detections. This geometric property can be represented by a spatial constellation model among the landmarks. The evaluation of matching between a landmark and the model can be determined by the spatial relationship between the landmark and other landmarks, i.e. how consistent the landmark is according to other landmarks.

According to the systems and methods of the present disclosure, a local voting algorithm is used to sequentially remove false detections until a predetermined number of local features remain. The main idea is that each detected landmark is considered as a candidate and the quality of a candidate is voted upon by voting groups formed by other landmarks. A higher vote means the candidate is more likely to be a good local feature.

---

Algorithm 1 Weakest-link removal (Min-Max) algorithm for each candidate $x_i$ do
    for each combinations of $X\setminus x_i$ do
        Compute the vote of $x_i$
    end for
    Sort all the votes received by landmark $x_i$. (The sorted array
    is defined by $\gamma_{x_i}$).
end for
repeat
    $\check{x} = \arg\min_{x_i} \max \gamma_{x_i}$
    Remove $\check{x}$ and all votes involved with $\check{x}$.
until Only M candidates are left

---

In general, this reasoning strategy "peels away" erroneous detections in a sequential manner. Each candidate receives a set of votes from other candidates. The reasoning strategy shown in algorithm 1 above then iteratively removes the worst candidate, i.e. the candidate whose maximum vote is the worst compared with the other candidates. This process repeated until the number of the remaining candidates reaches a pre-set value M. Assuming that there are at least M good candidates, all the bad candidates can be removed by this strategy.

The vote received by candidate $x_i$ is denoted by $h(x_i|X_v)$, where $x_v$ is a voting group. The vote is defined as likelihood between candidate $x_i$ and its prediction $n_i$ coming from the voting group. The likelihood function is modeled as multivariant Gaussian as following $$h(x_i \mid X_v) = \frac{1}{(2p)^{\frac{N}{2}} |S|^{\frac{1}{2}}} e^{-(x_i - n_i)^T S^{-1}(x_i - n_i)} \quad (1)$$

where S is the covariance matrix, and the prediction $n_i = q(x_i|X_v)$. Here q is a linear prediction function learned from a training set.

The number of detected landmarks for each image class is divided by the total number of detectors for that class, representing the final classification score. Depending on the classification task, a false positive reduction module may also be used in case that the classification score is lower than a pre-defined threshold. The reason is that images from OTHER class may have a small number of local patches with similar appearance as the defined image class, yet their spatial configuration is strong enough to pass the SCF stage. Therefore, the systems and methods of the present disclosure can optionally include an integrated post-filtering component based on global features to reduce the false positive identifications with similar local patches. The classifier used is preferably 1NN with Euclidean distance as similarity measurement, Experiments and Results To test the performance of the approach of the present disclosure, tests were run on four subtasks: PA-AP/LAT chest image view identification task with and without to OTHER class, and the multi-class medical image annotation task with and without OTHER class. For the chest image identification task, a large-scale in-house database was used, and for the multi-class radiograph annotation task, the IRMA/ImageCLEF2008 database was used.

The in-house image database was collected from daily routine from radiology departments in hospitals, containing total 10859 radiographs including total 5859 chest radiographs and 5000 other radiographs from a variety of other anatomy classes. The chest images covers a large variety of chest exams, representing image characteristics from real world PACS. 500 PA-AP, 500 LAT, and 500 OTHER images were randomly selected for training landmark detectors, and the remaining images were used as testing set.

For the multi-class medical radiograph annotation task, the IRMA/ImageCLEF2008 database was used. This database contains more than 10,000 images from total 197 unique classes. The distribution of different classes in this database is not uniform. The top nine classes comprised about 54% of the total images. A subset of images was selected from this database, containing PA-AP Chest, LAT Chest, PA-AP Left Hand, PA-AP Cranium, PA-AP Lumbar Spine, PA-AP Pelvis, LAT Lumbar Spine, PA-AP Cervical Spine, and LAT left to right Cranium. The remaining images were regarded as one OTHER class. The detectors for chest images for the previous task were used. For the remaining 7 classes, 200 images for each class were randomly selected. 150 images were used for training, and the remaining 50 images were used for testing. 2000 images were used for training and testing for OTHER category. All images were down-scaled to have a longest edge of 512 pixels while preserving aspect ratio.

For the two class PA-AP/LAT classification task, the systems and methods of the present disclosure were compared with known methods. For example, one method, proposed by Lehmann, involved a method using down-scaled image pixels with four distance measures along with K nearest neighbor (KNN) classifier. Another known method, proposed by Boone, involved using a neural network (NN) classifier working on down-sampled images.

For the multi-class radiograph classification task, the method of the present disclosure was compared to known methods and systems. In addition, the benchmark performance of a SVM classifier with linear kernel was also tested using 32×32 pixel intensity from the down-sampled image as a feature vector. Regarding Tommasi's method, the same modified SIFT descriptor was implemented. A SVM classifier with linear kernel directly combining 32×32 pixel intensity features and the modSIFT bag-of-features was used.

TABLE 1

The performance on PA-AP/LAT/OTHER chest radiographs annotation task

|  | PA-AP/LAT | PA-AP/LAT/OTHER |
|---|---|---|
| The method of the present disclosure | 99.98% | 98.81% |
| Our method without FP reduction | — | 98.47% |
| Lehmann's method | 99.04% | 96.18% |
| Boone's method | 98.24% | — |
| Improved Projection Profile method | 97.60% | — |

TABLE 2

The performance on multi-class radiographs annotation task

|  | Mutli-class without OTHER | Multi-class with OTHER |
|---|---|---|
| The method of the present disclosure | 99.33% | 98.81% |
| Subimage pixel intensity + SVM | 97.33% | 89.00% |
| SIFT + BOW + SVM | 98.89% | 95.86% |
| Patch + BOW + SVM | 96.89% | 94.71% |

Figure 7:
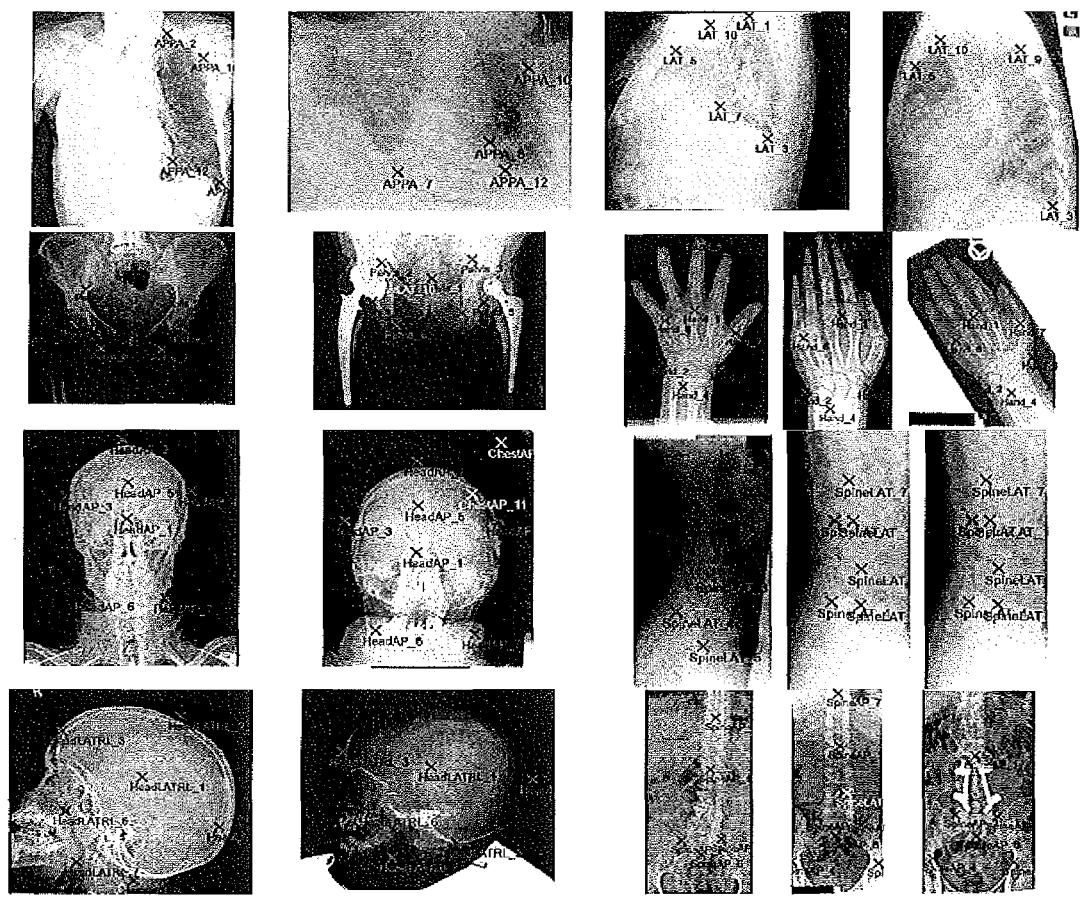
FIG. 7 is a set of exemplary radiographs including annotations created according to an embodiment of the present disclosure.

Table 1 and Table 2 above show the recognition rate of the method of the present disclosure, along with other methods. It can be seen that the method and system of the present disclosure has obtained almost perfect performance on the PA-AP/LAT separation task. The method of the present disclosure also performed the best on the other three tasks. FIG. 7 shows the classification result along with the detected landmarks for different classes. It can be seen that our method could robustly recognize challenging cases under the influence of artifacts or diseases.

In this systems and methods according to the present disclosure, for testing purposes 11 landmarks and 12 landmarks were used for PA-AP and LAT chest images. As for the other image classes, 7-9 landmarks were used. These are merely exemplary numbers and other numbers of landmarks could be used. In testing the systems and methods of the present disclosure 100 PA-AP and LAT images were annotated separately. Since the landmark detectors run on the Gaussian smoothed low resolution images, the detected position could deviate from the annotated ground truth position to certain degree, which is allowable for this medical image annotation application. It was determined that the detected landmark was a true positive detection when the distance between the detected position and the annotated ground truth position was smaller than 30 pixels. The detection performance can be traded off against computational time. In order to achieve real-time performance, an average sensitivity for the 23 chest landmark detectors at 86.91% (±9.29%), was deemed acceptable and was good enough to support the aforementioned overall system performance.

TABLE 3

The Performance of Landmark Detectors Before and After Voting

|  | FP reduction |
|---|---|
| 200 PA-AP/LAT | −55 |
| PA-AP/LAT/OTHER | −921 |
| Multi-Class with OTHER | −475 |

Figure 8:
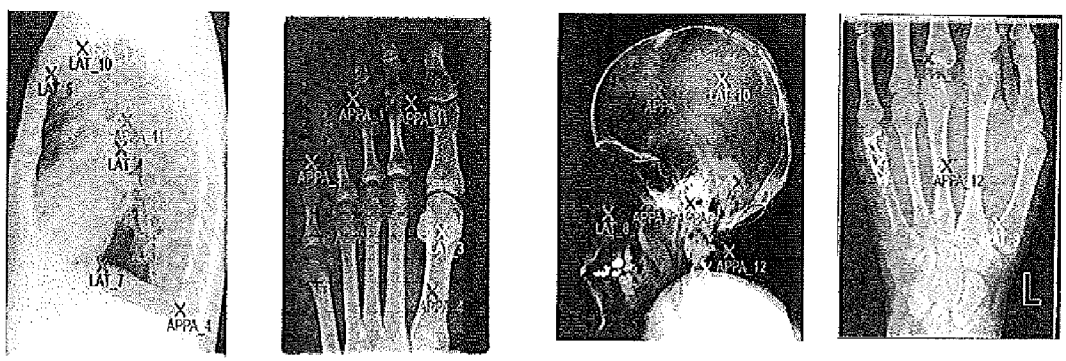
FIG. 8 is a set of medical images that may be used for automatic annotation according to an embodiment of the present disclosure.

Table 3 above shows the specificity of the landmark detectors before and after voting. The first row shows the result of PA-AP/LAT separation task on the 200 image subset with annotated landmark ground truth. 55 false positive detections out of 356 false positive landmark detections were filtered, which consisted of about 15.6% of all the false detections, while the true positive detection was unaffected. The second and the third row show the specificity performance on the PA-AP/LAT/OTHER separation task and the multi-class annotation task. Without the ground truth landmark annotated, all detected landmarks within the right image category were regarded as true positive detections. FIG. 8 shows the voting effect on different classes of images (a) LAT image, (b), (c) and (d) non chest images. The landmarks representing true positive detections are colored blue (darkest in FIG. 8); the landmarks representing false positive detections are colored yellow (lightest in FIG. 8); and the landmarks filtered by the voting algorithm are colored red (medium in FIG. 8).

The present disclosure proposes a learning-based approach for parsing and annotation of medical image. The disclosed approach has the advantage of quickly and robustly identifying images with considerable patient variance and under strong influence of disease or artifacts. Experiment results on a Chest X-ray view position identification and a multi-class radiograph annotation task has demonstrated the effectiveness and efficiency of this method. Additionally, due to the generality and scalability of the presently disclosed approach, this approach has the potential to annotate more image classes from other categories and on other image modalities.

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

Figure 4:
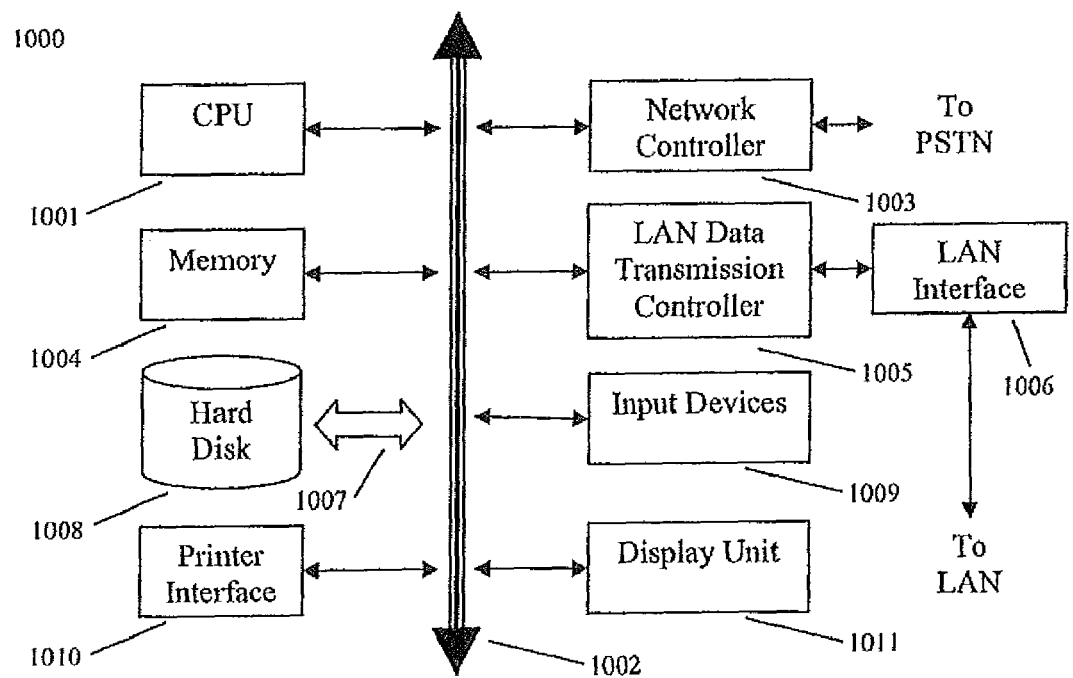
FIG. 4 shows an example of a computer system capable of implementing the method and apparatus according to embodiments of the present disclosure.

FIG. 4 shows an example of a computer system which may implement a method and system of the present disclosure. The computer system referred to generally as system 1000 may include, inter cilia, a central processing unit (CPU) 1001, memory 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

The memory 1004 can include random access memory (RAM), read only memory (ROM), disk drive, tape drive, etc., or a combinations thereof. The present invention can be implemented as a routine that is stored in memory 1004 and executed by the CPU 1001. As such, the computer system 1000 is a general purpose computer system that becomes a specific purpose computer system when executing the routine of the present invention.

The computer system 1000 also includes an operating system and micro instruction code. The various processes and functions described herein can either be part of the micro instruction code or part of the application program or routine (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A method for locating a region of interest within at least one preliminary scan, comprising:
    acquiring at least one preliminary scan;
    automatically detecting a set of local feature candidates from the at least one preliminary scan;
    assessing the accuracy of each local feature candidate using multiple combinations of the other local feature candidates and removing one or more local feature candidate that is assessed to have the lowest accuracy;
    locating a region of interest (ROD) from within the at least one preliminary scan based on the remaining number of local feature candidates.

2. The method of claim 1, wherein the at least one preliminary scan includes a scout image that includes a two-dimensional representation of a subject being scanned.

3. The method of claim 1, wherein assessing the accuracy of each local feature candidate is done iteratively, repeated until only a predetermined number of local feature candidates remains.

4. The method of claim 1, wherein the at least one preliminary scan includes at least one radiograph image.

5. The method of claim 1, wherein the local feature candidates represent potential anatomical landmarks or structures.

6. The method of claim 1, wherein the local feature candidates are automatically detected from the at least one preliminary scan by identifying regions of the at least one preliminary scan that appear to be known anatomical structures.

7. The method of claim 6, wherein the set of local feature candidates includes multiple local feature candidates that appear to be parts of the same anatomical structure.

8. The method of claim 1, wherein the accuracy of each local feature candidate is assessed by using each combination of other local feature candidates as a voting group, wherein each voting group votes for the each local feature candidate by judging the degree to which the each local feature candidate represents a corresponding local feature while assuming that the voting group accurately represents corresponding local features.

9. The method of claim 8, wherein each voting group includes 1, 2 or 3 other local feature candidates.

10. The method of claim 8, wherein each voting group includes 4 or more other local feature candidates.

11. The method of claim 1, wherein locating a region of interest (ROI) from within the at least one preliminary scan based on the remaining number of local feature candidates includes using the remaining number of local feature candidates as frame of reference to structurally register the at least one preliminary scan with a model scan in which the ROI has been delineated and then finding the region of interest (ROI) within the at least one preliminary scan based on the structural registration.

12. The method of claim 1, wherein each of the multiple combinations of the other local feature candidates comprises a voting group that votes for each local feature candidate in assessing their accuracy and for each iteration of repeating the assessing and removing step, a local feature candidate is assessed to have the lowest accuracy when its highest vote received by each of the multiple combinations of the other local feature candidates is the lowest among all local feature candidates.

13. The method of claim 1, wherein for each iteration of repeating the assessing and removing step, a local feature candidate is assessed to have the lowest accuracy when it is has a sudden reduction in vote value, as determined by examining the mean of good votes from a most recent iteration.

14. A method for annotating a medical image, comprising:
receiving a medical image;
automatically detecting a set of local feature candidates from the medical image;
determining which of the local feature candidates represent a worst candidate by having a plurality of groups of the local feature candidates vote on each individual local feature candidate, and removing the worst candidate from the set of local feature candidates;
repeating the voting and removal such that one feature candidate is removed from the set at each iteration, until there are only a predetermined number of remaining feature candidates;
annotating the medical image to assign it one or more labels from a set of pre-defined labels.

15. The method of claim 14, wherein the one or more labels identify the location of each of the remaining feature candidates.

16. The method of claim 14, wherein the medical image is a radiograph image.

17. The method of claim 14, wherein voting is performed by using each combination of other local feature candidates as a voting group, wherein each voting group votes for the each local feature candidate by judging the degree to which the each local feature candidate represents a corresponding local feature wile assuming that the voting group accurately represents corresponding local features.

18. The method of claim 17, wherein the one or more labels are manually selected by a user.

19. The method of claim 14, wherein the one or more labels are selected from the group including: class labels including Posteroanterior/Anteroposterio (PA/AP), Lateral (LAT), and anatomical structure labels including pelvis, spine, leg, hand, brain, hip.

20. The method of claim 14, wherein the one or more labels are assigned to the medical image by:
comparing the remaining feature candidates to a database of model images in which feature candidates and corresponding labels are known;
structurally registering the medical image to a selected model image; and
assigning the one or more labels to the medical image based on the structural registration.

21. A computer system comprising:
a processor; and
a program storage device readable by the computer system, embodying a program of instructions executable by the processor to perform method steps for locating a region of interest within a medical image, the method comprising:
acquiring a medical image;
automatically detecting a set of local feature candidates representing potential anatomical landmarks from the medical image;
assessing the accuracy of each local feature candidate using multiple combinations of the other local feature candidates and removing a local feature candidate that is assessed to have the lowest accuracy;
repeating the assessing and removing step until only a predetermined number of local feature candidates remain;
locating a provided region of interest (ROI) from within the medical image based on the remaining predetermined number of local feature candidates.

* * * * *